United States Patent [19]

Albert et al.

[11] Patent Number: 4,590,289

[45] Date of Patent: May 20, 1986

[54] PROCESS AND APPARATUS FOR PRODUCING ALUMINIUM ALKOXIDES

[75] Inventors: Gert Albert; Manfred Kamps; Klaus Noweck, all of Brunsbüttel; Ansgar Reichenauer, Marne; Erich Scherf; Udo Ziegler, both of Brunsbüttel, all of Fed. Rep. of Germany

[73] Assignee: Condea Chemie GmbH, Brunsbüttel, Fed. Rep. of Germany

[21] Appl. No.: 556,112

[22] Filed: Nov. 29, 1983

[30] Foreign Application Priority Data

Dec. 4, 1982 [DE] Fed. Rep. of Germany ....... 3244972

[51] Int. Cl.$^4$ .............................................. C07F 5/06
[52] U.S. Cl. .................................... 556/188; 422/189
[58] Field of Search ................. 260/448 AD; 422/189

[56] References Cited

U.S. PATENT DOCUMENTS

| | | | |
|---|---|---|---|
| 2,666,076 | 1/1954 | Rex et al. | 260/448 AD |
| 2,845,447 | 7/1958 | Carlson et al. | 260/448 AD |
| 2,965,663 | 12/1960 | Smith et al. | 260/448 AD |
| 3,094,546 | 6/1963 | Towers | 260/448 AD |
| 3,446,828 | 5/1969 | Buzas et al. | 260/448 AD |
| 4,187,254 | 2/1980 | Bujadoux et al. | 260/448 AD X |
| 4,242,271 | 12/1980 | Weber et al. | 260/448 AD |

FOREIGN PATENT DOCUMENTS 930087 7/1955 Fed. Rep. of Germany .

Primary Examiner—Helen M. S. Sneed
Attorney, Agent, or Firm—Cushman, Darby & Cushman

[57] ABSTRACT

The invention is directed to a process for the production of aluminium alcoholates by reacting aluminium in comminuted form with an excess of an aliphatic $C_3$ to $C_{10}$ alcohol in which the aluminium is supplied to the reactor from above and is brought into contact with an aluminium alcoholate/alcohol mixture above a perforated plate or grid tray (screen) in the reactor. The aluminium, or preferably a suspension of alcohol and finely divided aluminium, is supplied to the reactor and fed from above to a bubble bed made of a mixture of aluminium alcoholate and alcohol in the area of the perforated plate, whereby the mixture of aluminium alcoholate and alcohol in the reactor sump or overflowing in part is recycled to the reactor over the bubble bed and optionally, preferably with the aluminium suspension, returned from above to the reactor and in part is isolated. There is also described a reactor suitable for carrying out the process. The reactor has a basket like perforated plate in a tray and inlet lines for maintaining a sufficient amount of liquid in the tray or the bubble bed above the perforated plate or grid tray.

19 Claims, 1 Drawing Figure

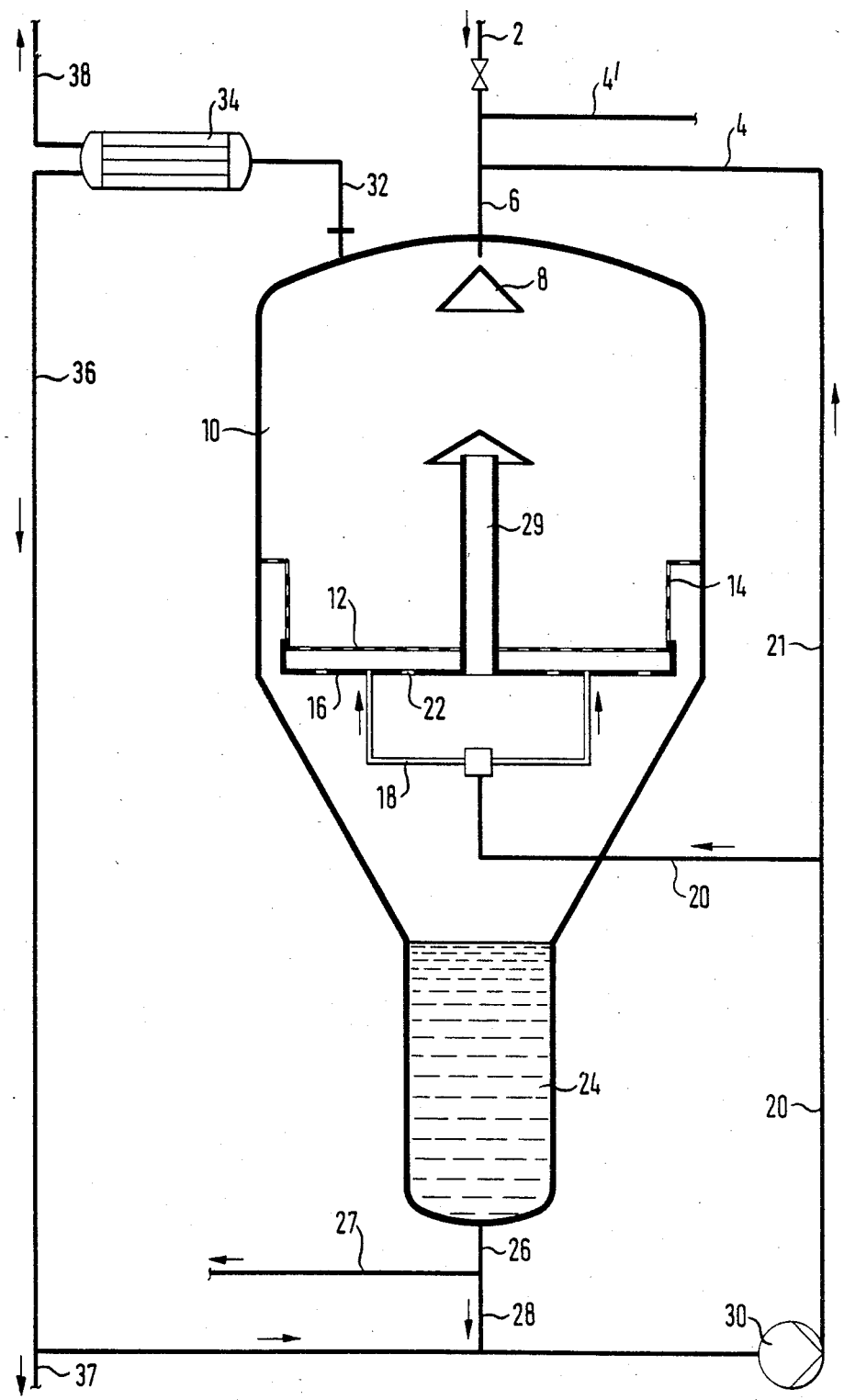

PROCESS AND APPARATUS FOR PRODUCING ALUMINIUM ALKOXIDES

BACKGROUND OF THE INVENTION

The invention relates to a continuous process for producing aluminium, e.g. alkoxides by reacting aluminium in comminuted form with an excess of aliphatic $C_3$ to $C_{10}$-alcohol, in which the aluminium being fed from above into a reactor is contacted on or above a perforated plate or screen with an aluminium alkoxide/alcohol mixture.

When reacting aluminium and anhydrous alcohol for producing metal alkoxides (also called alcoholates), due to the high heat of reaction occuring during this reaction, there are considerable problems both when reacting large quantities and when the process is performed continuously. Such problems are caused, for example, by unequal aluminium metering or due to the fact that part of the aluminium only reacts after a certain time, accompanied by the momentary release of large quantities of heat.

To eliminate these problems, U.S. Pat. No. 2,845,447 for example, proposes carrying out the reaction not with an excess of alcohol but with an excess of aluminium in the liquid phase. The aluminium in the reactor is contacted with a mixture of aluminium alkoxide and alcohol in the lower area of the reactor and the resulting aluminium alkoxide with the as yet unreacted alcohol is in part supplied back to the reactor circuit and in part is separated. In this process with excess aluminium, as a result of pressure fluctuations or for other reasons, suddenly larger quantities of the alcohol-aluminium alkoxide mixture can come into contact with the aluminium and consequently release large quantities of heat, which can overload the plant. In addition, lower reaction rates can result from working with substoichiometric alcohol quantities and as a result the yield is reduced.

Similar problems with respect to the reaction control occur in a process according to U.S. Pat. No. 2,666,076, in which working takes place with an excess of aluminium alkoxide/alcohol mixture in the reactor and aluminium granulate is continuously supplied from above into the said reactor.

In another but discontinuous process according to German Pat. No. 930,087, the aluminium is present in comminuted form on a screen plate of a reactor and is contacted with alcohol introduced into the reactor. When the reaction gets out of control the liquid phase is forced into an expansion vessel as a result of the hydrogen overpressure which occurs, so that the liquid phase is separated from the aluminium present on the screen plate. This process operates with an alcohol excess and in the case of a reverse flow of the liquid phase, there can be a reaction which is difficult to control and is excessive.

The object of the invention is to propose a process for producing aluminium alkoxides, which can be continuously performed in trouble-free manner with good yields and in which the liquid phase is immediately separated from the aluminium if a fault occurs. In addition, the process according to the invention, unlike the aforementioned and other known processes, makes it possible to use normal grade aluminium instead of aluminium activated by addition of further metals or metal compounds, and also pure alcohols can be used, i.e. the alcohol desired for alkoxide formation, without, as has often been proposed, having to introduce heavier hydrocarbons into the liquid phase for controlling the reaction, which ensures the purity of the end product.

SUMMARY OF THE INVENTION

To solve the present problem a method of the above-mentioned kind is proposed by which aluminium is supplied onto a bubble bed being produced in the area of a perforated plate or grid bottom (screen plate) from a mixture of aluminium alkoxide and alcohol whereby the overflowing or outflowing mixture of aluminium alkoxide and alcohol in the reactor sump is in part recycled into the reactor via the bubble bed while the other part is separated. The term screen is used herein to exclude generally perforated plates, grid trays and similar sieve like devices.

This method advantageously permits the bubble bed obtained by evaporation of the alcohol and development of hydrogen providing a good or thorough mixing of the reactants within the bubble bed which results in an immediate reaction. A further substantial advantage results from the fact that if faults occur, by interrupting the supply of aluminium alkoxide/alcohol mixture, the bubble bed immediately collapses and aluminium can be separated from the liquid reaction mixture.

Preferably, the aluminium is added into the reactor and onto the bubble bed in the form of a suspension of alcohol and finely divided aluminium. By this the addition of both reactants is made in a cold and thus not reactive suspension; this also enables adding a controlled addition of this suspension into the liquid phase which is kept at a reactive temperature so that it is possible to work with the best reaction rates due to the alcohol being present in superstoichiometric quantities.

This kind of controlled supply has the further advantage of being independent from the geometrical shape of the aluminium particles so that needles, filings, or granules can be used as the material employed.

Further, it is preferable to introduce a part of the recirculated mixture of aluminium alkoxide and alcohol into the reactor from above to obtain a more even reaction of aluminium with alcohol. For the same reason, it is an advantage if the suspension of alcohol and finely divided aluminium is introduced into the reactor via a nozzle together with additional alcohol and/or with a mixture of aluminium alkoxide/alcohol as a suspension. The supply of alcohol secures in the upper area of the bubble bed a sufficient source of alcohol which enables the achievement of higher reaction rates. To maintain the maximum effect of the bubble bed and to secure a uniform reaction, it is an advantage if the recirculated mixture of aluminium alcoholate and alcohol is fed into the reactor both from above and also via the bubble bed whereby the ratio of the volume being added from above to the volume added via the bubble bed is within the range of 1:2 to 1:4.

Further, it is an advantage if one supplies the reactor with 35 to 90 parts of volume of the overflowing mixture of aluminium alcoholate and alcohol while one part of volume is isolated as final product.

The invention also relates to an apparatus for performing this process, comprising a reactor with a grid tray or perforated plate (screen), a supply line for the reactants located in the upper area of the reactor and a discharge line subdivided into a return line to the reactor and into a product line, characterized in that below the perforated plate or grid tray is provided a tray with supply lines for the aluminium alkoxide/alcohol mixture and with drain holes and that the grid tray or perforated plate in the tank is constructed in basket-like manner having an all-round wall with perforations.

With respect to the supply lines for the aluminium alkoxide/alcohol mixture, the drain holes in the tray are preferably dimensioned in such a way that larger volume parts of the aluminium alkoxide/alcohol mixture pass into the tray than can drain out through the drain holes in the same period of time. This means that even in the case of a partly overflowing liquid phase, a bubble bed is always maintained by the larger quantity of aluminium alkoxide/alcohol mixture supplied. Preferably, 3 to 15 and especially 6 to 8 parts by volume of this mixture should be added to the bubble bed per one part of the aluminium alkoxide/alcohol mixture flowing out through the drain hole.

In the process according to the invention, the aluminium is used in conventional manner in comminuted form, e.g. in the form of needles, filings or granules, it being unnecessary to activated the aluminium by foreign metals.

The alcohols used can be aliphatic $C_3$ to $C_{10}$-alcohols and more particularly $C_5$ to $C_8$-alcohols with a straight-chain alkyl radical, e.g. n-propanol, n-butanol, n-pentanol, n-hexanol, n-heptanol, n-octanol and n-decanol.

BRIEF DESCRIPTION OF THE DRAWING

The invention is described in greater detail hereinafter relative to the attached drawing, which diagrammatically shows a section through the reactor according to the invention.

DETAILED DESCRIPTION

Finely divided aluminium is supplied via line 2 from a not shown storage tank either pneumatically or mechanically via a pressure lock or preferably as suspension of finely divided aluminium in the alcohol being used for the alcoholate formation by means of a pump or a liquid/liquid ejector; the suspension is supplied from a mixing tank with stirrer via supply line 6 into the reactor 10 which is under a slight excess pressure. The solids content of the aluminium suspension can be in a range of 5 to 50% by weight aluminium. Further alcohol and/or an aluminium alkoxide/alcohol mixture is supplied by means of separate lines 4 or 4' in the top area of supply line 6. For the better distribution of the aluminium suspension, distributor plates 8 are arranged below the discharge opening of supply line 6.

Reactor 10 contains a grid or perforated plate 12 having all-round walls 14 with corresponding perforations and which is fixed in suitable manner within the reactor. Below the perforated plate or grid tray, there is a tray 16 supplied with a mixture of aluminium alkoxide and alcohol by means of a plurality of supply lines 18 and by means of a distributor head from a line 20. The liquid mixture passing out of the distributing lines produces a bubble bed in the vicinity of grid tray 12 in which the reaction between the alcohol and the aluminium takes place.

The bottom of tray 16 has drain holes 22, whose passage surface, compared with that of the supply lines 18, is dimensioned in such a way that although part of the liquid phase flows downwards into the reactor from the bubble bed, there is still an adequate liquid phase excess in the tray to maintain the bubble bed. The aluminium alkoxide formed in the bubble bed together with the alcohol present, flows onwards and downwards through the opening in wall area 14 of the basket-like grid bed and through the perforated plate and outlet openings 22 in tray 16 into the sump. The mixture of alcohol and aluminium alkoxide collecting in the lower area of the reactor and which is enriched in aluminium alkoxide is drawn off by means of a line 26 and in part, optionally with fresh alcohol, is returned in line 20 via line 28 and pump 30 to the reactor or bubble bed and in part is supplied for further processing or recovery via line 27. The hydrogen formed during the reaction and the vaporized alcohol are fed via an exit line 32 to condenser 34 from which the condensed alcohol is drawn via line 36 to freshen up the aluminium alcoholate/alcohol mixture, which had been taken from the reactor sump 24, and is recirculated into the reactor via line 26 and 28 of the circulation pump 30. The alcohol can also be removed via a further line 37 and may be directly fed into the reactor from above or e.g. together with the aluminium suspension. The hydrogen obtained in the condensator and being freed from alcohol can be removed via line 38.

Line 20 is in connection with supply line 4 via a branch line 21 so that the mixture of aluminium alkoxide and alcohol can be fed into the reactor both via the bubble bed and from above into the reactor.

To avoid pressure differences between the upper and lower areas of the reactor, a preferably shielded pressure balancing pipe 29 is provided, which connects the lower area of the autoclave to the upper area.

If irregularities or faults occur in the performance of the reaction and which are made apparent by pressure or temperature fluctuations, the reaction can be interrupted by immediately switching-off the pump circulating the mixture of aluminium alkoxide and alcohol, whereby simultaneously it is possible to bring about an interruption of the supply of the aluminium/alcohol suspension by closing a valve in supply line 6. On closing the circulating pump the bubble bed immediately collapses. The liquid phase flows out through openings 22 into the lower part of the reactor and all that is left behind on the sieve tray is a small amount of aluminium from the previously supplied aluminium/alcohol suspension. This arrangement leads to a complete separation between the solid and liquid phases within 20 to 120 seconds in case of a fault.

With the process according to the invention, the bubble bed can be supplied with the aluminium alkoxide/alcohol mixture obtained or with a mixture enriched with fresh alcohol or only with said alcohol. Supply line 6 can also supply either pure alcohol or an alcohol already containing aluminium alkoxide. If part of the branched off circulating flow is mixed with the aluminium suspension and is introduced from above into the reactor, there is simultaneously a preheating of the fresh quantity supplied by the rising alcohol vapours.

After a fault or on discontinuing the reactor, there is no need to open and clean the letter, because it can be operated with the circulating fluid and alcohol until the aluminium remaining there in the sieve tray is consumed and then once again fresh aluminium/alcohol suspension can be added.

EXAMPLE 1

A reactor of steel as described above and having a capacity of 3 $m^3$ and a diameter within the sieve (perforation) area of 0.84 m was used. An amount of 110 kg aluminium needles having a thickness of 0.4 to 0.6 mm and a length of about 4 to 6 mm were added per hour and per m² performated plate area together with 13.6 kg hexanol per kg aluminium. An amount of 0.83 m³ of the mixture of aluminium alcoholate and alcohol were added into the reactor per hour and per kg aluminium by circulation. The addition was made both via the upper supply line 4 and also via supply line 20 whereby the ratio of the added amounts was 1:3. The pressure of the reactor was 1.3 bar.

The bubble bed formed on the perforated plate under these reaction conditions had a height of about 15 cm and a temperature of about 175° C. The yield of aluminium alcoholate based on the use of aluminium was about 99.4%.

At a simulated fault all dosing devices and the circulating pump were shut-off and after a period of 30 seconds the entire liquid phase had flown from the sieve bottom into the lower area of the reactor.

EXAMPLE 2

It was worked analogously as in Example 1, whereby, however, the necessary mixture of aluminium alkoxide and alcohol was supplied only via line 20 to the tank 16 and the bubble bed. The yield of aluminium alkoxide was about 99.1% based on the aluminium used. However, only 100 kg aluminium per m³ perforated plate an hour could be reacted.

EXAMPLE 3

Aluminium granules were introduced via a dosing apparatus from above into a pilot reactor similar in structure to the reactor used in Example 1. An amount of 0.84 m³ of the mixture consisting of aluminium alkoxide and alcohol were introduced per hour and per kg aluminium used and circulated, however, only via the lower supply line 20. The pressure of the reactor was 0.3 bar gauge. The temperature in the bubble bed was about 175° C.

When using 13.6 kg hexanol per kg aluminium a yield of 99.3% aluminium alcoholate based on aluminium was obtained. However, only 98 kg granules per m³ sieve bottom an hour could be reacted.

The entire disclosure of German priority application No. P 3244972.0 is hereby incorporated by reference.

What is claimed is:

1. A process for the continuous production of an aluminium alkoxide comprising:
   reacting aluminium alcohol in a reactor, said process including:
   supplying the aluminium to the reactor from above;
   supplying alcohol to said reactor;
   contacting the aluminium with an aluminium alkoxide/alcohol mixture in the form of a bubble bed above a screen in the reactor;
   in part recycling to the reactor above the bubble bed overflowing and outflowing aluminium alkoxide and alcohol from the sump of the reactor; and
   separating off another portion of the aluminium alkoxide and alcohol, said process including means for controllably interrupting the supply of aluminum, alcohol and the recycling of aluminum alkoxide and alcohol to said reactor.

2. A process according to claim 1 comprising adding the aluminium to the reactor and onto the bubble bed as a suspension of alcohol and finely divided aluminium.

3. A process according to claim 2 comprising adding the suspension of finely divided aluminium and alcohol via a nozzle together with additional alcohol or a mixture of alcohol and aluminium alkoxide as a suspension.

4. A process according to claim 3 wherein a portion of the recycling mixture of aluminium alkoxide and alcohol is supplied to the reactor from above.

5. A process according to claim 1 wherein a portion of the recycling mixture of aluminium alkoxide and alcohol is supplied to the reactor from above.

6. A process according to claim 5 wherein the recycling mixture of aluminium alkoxide and alcohol is supplied to the reactor both from above and also via the bubble bed, the ratio of the portion supplied above to the portion supplied via the bubble bed is 1:2 to 1:4 parts by volume.

7. A process according to claim 4 wherein the recycling mixture of aluminium alkoxide and alcohol is supplied to the reactor both from above and also via the bubble bed, the ratio of the portion supplied above to the portion supplied via the bubble bed in 1:2 to 1:4 parts by volume.

8. A process according to claim 7 wherein for each 35 to 90 parts by volume of the overflowing mixture of aluminium alkoxide and alcohol supplied to the reactor 1 part by volume of product is isolated.

9. A process according to claim 6 wherein for each 35 to 90 parts by volume of the overflowing mixture of aluminium alkoxide and alcohol supplied to the reactor 1 part by volume of product is isolated.

10. A process according to claim 5 wherein for each 35 to 90 parts by volume of the overflowing mixture of aluminium alkoxide and alcohol supplied to the reactor 1 part by volume of product is isolated.

11. A process according to claim 4 wherein for each 35 to 90 parts by volume of the overflowing mixture of aluminium alkoxide and alcohol supplied to the reactor 1 part by volume of product is isolated.

12. A process according to claim 3 wherein for each 35 to 90 parts by volume of the overflowing mixture of aluminum alkoxide and alcohol supplied to the reactor 1 part by volume of product is isolated.

13. A process according to claim 2 wherein for each 35 to 90 parts by volume of the overflowing mixture of aluminium alkoxide and alcohol supplied to the reactor 1 part by volume of product is isolated.

14. A process according to claim 1 wherein for each 35 to 90 parts by volume of the overflowing mixture of aluminium alkoxide and alcohol supplied to the reactor 1 part by volume of product is isolated.

15. An apparatus suitable for the continuous production of an aluminium alkoxide by reacting aluminum in comminuted form with an excess of a $C_3$ to $C_{10}$ alcohol comprising:
   a reactor having basket-like screening means,
   supply line means for supplying reactants in the upper area of the reactor above the screening means,
   control means for controllably interrupting the supply of reactants to said reactor and for controllably interrupting the recirculation of reactants and reaction products,
   discharge line means for discharging the reactor, said discharge line means extending from the lower area of the reactor below the screen means, said discharge line means being subdivided into a return line to the reactor and a product line below the screening means there being provided a tray means having a supply line means for the aluminium alkoxide-alcohol mixture and having drain holes, the basket-like screening means having an all-round perforated wall.

16. An apparatus according to claim 15 wherein the drain holes in the tray in relation to the supply line means for the aluminium alkoxide-alcohol mixture being so dimensioned that for each part of the overflowing aluminium alkoxide-alcohol mixture flowing out through the drain hole 3 to 15 parts by volume of the mixture can be added to the bubble bed.

17. A process according to claim 8 wherein 3 to 15 parts by volume of aluminum alkoxide/alcohol mixture is added to the bubble bed per one part of aluminum alkoxide/alcohol mixture removed from the sump.

18. A process according to claim 17 wherein 6 to 8 parts by volume of aluminum alkoxide/alcohol mixture is added to the bubble bed per one part of aluminum alkoxide/alcohol mixture removed from the sump.

19. A process according to claim 14 wherein 3 to 15 parts by volume of aluminum alkoxide/alcohol mixture is added to the bubble bed per one part of aluminum alkoxide/alcohol mixture removed from the sump.

* * * * *